(12) United States Patent
Li

(10) Patent No.: US 8,414,937 B2
(45) Date of Patent: Apr. 9, 2013

(54) CHINESE MEDICINE COMPOSITION FOR TREATING CANCER

(76) Inventor: Aiying Li, Yantai (CN)

( * ) Notice: Subject to any disclaimer, the term of this patent is extended or adjusted under 35 U.S.C. 154(b) by 0 days.

(21) Appl. No.: 13/292,395

(22) Filed: Nov. 9, 2011

(65) Prior Publication Data

US 2013/0064898 A1    Mar. 14, 2013

(30) Foreign Application Priority Data

Sep. 9, 2011  (CN) .......................... 2011 1 0280960

(51) Int. Cl.
 *A61K 36/00*    (2006.01)
(52) U.S. Cl.
 USPC ........................................................ 424/725
(58) Field of Classification Search .................. None
 See application file for complete search history.

(56) References Cited

PUBLICATIONS

Jagannath, S. "Types of Treatment" Cancer.Net. Web Date: Nov. 18, 2011. [Retrieved from the Internet on: Oct. 17, 2012]. Retrieved from: <http://www.cancer.net/all-about-cancer/treating-cancer/types-treatment>.*

* cited by examiner

*Primary Examiner* — Amy L Clark
(74) *Attorney, Agent, or Firm* — Venable LLP; Robert Kinberg

(57) ABSTRACT

A composition for treating tumors caused by pancreatic, stomach, breast, or liver cancer, leukemia, lung or liver metastasis, and/or arterial aneurysm. The composition comprises in various parts: turtle shell, radix ranunculi ternati, rhizoma dioscoreae bulbiferae, concha arcae, fructus ligustri lucidi, cordyceps sinensis, dwarf lilyturf tuber, Whim brownii, radix astragali, angelica sinensis, radix pseudostellariae, spina date seed, fruit-spike of common selfheal, pericarpium citri reticulatae, costustoot, cape jasmine fruit, radix scrophulariae, radix rehmanniae, rhizoma corydalis, safflower, turmeric root-tuber, cortex moutan, concha ostreae, poria cocoa, herba lysimachiae, the root of red-rooted salvia, isatis indigotica fort, honeysuckle, fructus forsythiae, cortex eucommiae, radix gentianae macrophyllae, radix paeoniae alba, subprostrate sophora, seman platycladi, snakegourd fruit, membrane of chicken gizzard, platycodon grandiflorum, and radix liquiritiae.

2 Claims, No Drawings

CHINESE MEDICINE COMPOSITION FOR TREATING CANCER

CROSS REFERENCE TO RELATED APPLICATIONS

This application claims the priority of Chinese Application No. 201110280960.4, filed Sep. 9, 2011, the disclosure of which is incorporated herein by reference in its entirety.

FIELD OF THE INVENTION

The present invention relates to a Chinese medicine composition, and particular to a Chinese medicine composition for treating a cancer.

BACKGROUND OF THE INVENTION

A cancer is the most common malignant tumor in clinic, and has a high incidence in various countries around the world. Common clinical cancers include a liver cancer, a stomach cancer, a lung cancer, a breast cancer, a leukemia, a pancreatic cancer, a bladder cancer, a uterine cancer, a lymphoma, a bone cancer, etc. For the above various types of cancers, there is no obvious symptom in the early stage. Since most cancers have been in the late stage when symptoms appear, delayed diagnosis happens very likely. The common clinical manifestations of the cancers include a loss of appetite, low fever, a weight loss, a pale face, anemia, weakness, edema and other systemic cachexia performance. At present, a cancer can be clinically treated in many ways. If a cancer is detected in the early stage, a surgery way is possible for treating the cancer, for example, surgical resection is the best way for treating early cancer. However, the surgery way can only prolong life, and many patients relapse in 2-5 years and suffer from a late cancer. Patients in the late stage can be treated depending on their own conditions. Patients in good physical conditions suitable for surgical treatment usually choose the surgery way. However, depending on the disease, those who are not suitable for surgery can merely select treatment options including chemotherapy, a radiation therapy, a hemodialysis therapy, a therapy using imported medicines, a therapy using Chinese medicine, etc. The above treatment options all aim to prolong life. Some patients can extend their own lives for a few years and months by certain treatment, while conditions of many other patients are not improved, get worsened or even die soon after the treatment through the above treatments, because of side effects of chemotherapy, radiotherapy, hemodialysis therapy, surgery. There are also many patients who cannot stand the pain caused by radiotherapy, chemotherapy, surgery and the hemodialysis therapy and give up treatment, as a result, they quickly lose their lives. There are also many patients who cannot afford the therapy and choose to give up life. Therefore, the cancer is indeed the enemy of mankind and seriously endangers the life and health of people around the world.

SUMMARY OF THE INVENTION

An object of the present invention is to provide a Chinese medicine composition for treating a cancer. The inventive medicine composition has instant and significant effects, making a patient improve quickly in conditions and restore fast in physical strength. Further, the medicine can cure the patients fast with a high cure rate, without pain or side-effect during the treatment.

To obtain the forgoing object, there is provided such a technical solution as follows. A Chinese medicine composition for treating a cancer prepared from Chinese medicines comprising by weight: 10-30 parts of turtle shell, 15-30 parts of radix ranunculi rernati, 10-15 parts of rhizoma dioscoreae bulbiferae, 10-30 parts of concha arcae, 10-15 parts of fructus ligustri lucidi, 10-15 parts of cordyceps sinensis, 10-15 parts of dwarf lilyturf tuber, 10-30 parts of lilium brownii, 10-15 parts of radix astragali, 5-10 parts of angelica sinensis, 10-30 parts of radix pseudostellariae, 10-18 parts of spina date seed, 10-15 parts of fruit-spike of common selfheal, 3-10 parts of pericarpium citri reticulatae, 3-10 parts of costustoot, 3-10 parts of cape jasmine fruit, 10-15 parts of radix scrophulariae, 10-30 parts of radix rehmanniae, 5-10 parts of rhizoma corydalis, 5-10 parts of safflower, 6-12 parts of turmeric root-tuber, 6-12 parts of cortex moutan, 10-30 parts of concha ostreae, 10-15 parts of poria cocos, 30-60 parts of herba lysimachiae, 5-15 parts of the root of red-rooted salvia, 10-15 parts of isatis indigotica fort, 10-15 parts of honeysuckle, 6-15 parts of fructus forsythiae, 10-15 parts of cortex eucommiae, 5-10 parts of radix gentianae macrophyllae, 15-30 parts of radix paeoniae alba, 6-10 parts of subprostrate sophora, 10-18 parts of seman platycladi, 10-20 parts of snakegourd fruit, 5-10 parts of membrane of chicken gizzard, 5-10 parts of platycodon grandiflorum, and 5-10 parts of radix liquiritiae.

The above Chinese medicines can be formulated into solution according to conventional methods.

The turtle shell, radix ranunculi ternati, rhizoma dioscoreae bulbiferae, and concha arcae used in the present invention have the effects of resolving hard lump, dissipation of the tumor, and inhibition of proliferation of cancer cells, etc.; fructus ligustri lucidi, cordyceps sinensis, dwarf lilyturf tuber, and lilium brownii have the effects of tonifying the liver and kidney, moistening heart and lung, stabilizing the five internal organs and so on; radix astragali, angelica sinensis, radix pseudostellariae, spina date seed have the effects of vitality and nourishing, strengthening the spleen, tranquilizing the mind and so on; fruit-spike of common selfheal, pericarpium citri reticulatae, costustoot, and cape Jasmine Fruit have the effects of soothing the liver and regulating the Qi, promoting Qi circulation and tuning, and so on; radix scrophulariae, radix rehmanniae, concha ostreae, and platycodon grandiflorum have the effects of heat dissipation and nourishing Yin, moistening the lungs and generating saliva, reducing phlegm and relieving swelling, resolving hard lump and so on; rhizoma corydalis, safflower, turmeric root-tuber, cortex moutan have the effects of promoting blood circulation, promoting Qi circulation and relieving pain, and so on; poria cocos, herba lysimachiae, and the root of red-rooted salvia have the effects of smoothening waterways, diuresis, reducing swelling and relieving pain, and so on; subprostrate sophora, isatis indigotica fort, honeysuckle, and fructus forsythiae have the effects of heat dissipation and detoxification, reducing swelling and easing pain, and so on; cortex eucommiae, radix gentianae macrophyllae, and radix paeoniae alba have the effects of tonifying the liver and kidney, strengthening bones and tendons, and so on; seman platycladi, snakegourd fruit, and membrane of chicken gizzard have the effects of facilitating digestion and nourishing the stomach, and so on; and radix liquiritiae has the efficacy of regulating herbal property.

The Chinese medicines are used in their appropriate amounts in the invention and form a unique formulation. Through a variety of drug interactions, these medicines are complementary and mutually beneficial, resulting in the effects of resolving hard lump, dissipation of the tumor, tonifying the liver and kidney, moistening heart and lung, benefiting the spleen and stomach, stabilizing the five internal organs, enriching Qi and blood, soothing the liver and regulating Qi, generating saliva and reducing phlegm, detoxification and removing stasis, promoting urination and bowel movements, detumescence and odynolysis and so on. Clinically, it is concluded from the treatment of 55 cancer patients that: the present invention has a significant effect on various patients who suffer a cancer in different body parts. Whether the cancer is in the early, middle or late stage, and regardless of how seriously the cancer spreads in advanced patients, as long as the patients can eat and drink, their gastric digestion and absorption functions are well, their digestive systems are smooth, as well as medicine drunk into their stomachs can be absorbed instead of being spit out, symptoms will certainly begin to reduce, the conditions will begin to less severe, and cancer cells can be suppressed from proliferating, after a few or ten days after the drug administration. In about 15 days, the symptoms are significantly alleviated, the conditions are improved significantly, cancer cells begin to be eliminated, and tumors begin to shrink. In about 2-3 months, systemic symptoms may disappear, the conditions can be fully alleviated, cancer cells disappear basically or completely, and the tumor is eliminated basically or completely. Accordingly, for a variety of cancer patients who take the medicine composition according to the invention, since cancer cells can be eliminated magically in a few months, the cancer patients can be raised from death and receive a second chance of life. The Chinese medicine composition according to the invention has the following five major advantages: 1) the composition has instant effects and a high effective rate (e.g. 100%), and may be effective in about 3-5 days, with increased diet, unobstructed stool and urine, improvement of sleep and edema, etc.; 2) patient's condition is improved quickly, specifically, almost all symptoms can be improved in about 15 days, that is, edema can be significantly subsided, pain is reduced significantly, cancer cells have been suppressed, and the tumor begins to shrink, etc.; 3) physical strength restores fast, specifically, patient looks better in about 1-2 months with a weight gain and resumption of strength, and can work, study and live just like a person in good condition; 4) patients can be cured fast with a high cure rate, the present medicine composition can eliminate the tumor and kill the cancer cells, thus curing the patients with a cure rate up to 98% in 3-5 months; And 5) treatment is easy and painless, that is, the present invention is directed to a pure Chinese medicine composition, which is easy to take and causes no pain during treatment, without side-effect. Clinical trials have concluded that: the size of cancer is not directly proportional to the number of the survival cancer cells, thus the cancer cells may be not completely eliminated, while the tumor completely disappears. Consolidation therapy is required to continue for about 1-2 months after the tumor has been completely eliminated, then the administration of the medicine may be discontinued. After clinical validation, tumor may be dissipated by 1.2-1.8 cm after the administration of the traditional Chinese medicine composition according to the present invention for about one month, and this shows that the dissipation of cancer varies from person to person. For example, for young patients and patients in strong physical conditions whose cancer has not spread and who have not conducted surgery and chemotherapy, the cancer will be eliminated faster, while for the elderly and patients in weak physical conditions whose cancer has spread and who have conducted surgery, radiotherapy and chemotherapy, the cancer will be eliminated slower. Also, it has been concluded in the course of treatment that: the Chinese medicine composition of the invention is effective in every cancer and can cure various cancer patients quickly with short treatment time, without pain or side effect during the treatment.

Hereinafter, a few typical cases of advanced cancer are provided to further illustrate the therapeutic effects of Chinese medicine composition according to the invention.

Case 1.

Wang Shu-Zhen, female, 65 years old, lived in Qingyang street office, Fushan District, Yantai, Shandong Province. She went to a large hospital in Beijing for examination on Feb. 3, 2009, and a CT scan and pathology indicated that there was a hypoechoic mass of a size of 4.8 cm×4.6 cm at uterine endometrial gland tail with unclear boundary, along with liver and lung metastasis. Finally, she was diagnosed with advanced pancreatic cancer complicated by liver and lung metastasis at multiple sites. It has been impossible to conduct a surgery and chemotherapy, only by injection of nutrient solution and the use of painkillers can she extend life for only 2-3 months. Her family felt very sad when they heard of the news from the doctor, and then tried to look around for the recipe for treating the cancer from Chinese medicine. Finally on Apr. 31, 2009, she found and decided to use the Chinese medicine according to the invention for treatment. A miracle appeared only on the third day after drug administration, that is, she can eat. On the fourth day, she could relieve herself unobstructed, and increased urine output. On the fifth day, the edema began to subside, and on the seventh day the pain began to reduce and her sleep got better. 10 days later, her appetite began to improve and bowel movements began to be regular. 18 days later she could get out of bed and do proper exercise. Since then, her condition was gradually improved. Two months later, she looked health and gained 2.5 kg of weight. Also she restored strength to do housework, and all symptoms of her body basically disappeared except that she had vague abdominal pain occasionally. She went to the hospital and accepted ultrasonic testing, the results showed there was a hypoechoic mass of the size of 1.9 cm×2.0 cm at uterine endometrial gland tail with unclear boundaries, and liver, gallbladder, lung, spleen and kidneys were normal. After treatment with the medicine of the invention for further two months, the ultrasonic testing showed the pancreas was in normal size and shape. Two months of consolidation therapy later, the medicine-taking was discontinued. She fully recovered after a total of six months of treatment, and in the whole course of treatment, no side effects occurred. It has been two years so far, she has been in good physical condition.

Case 2.

Pan Ming-Jiu, male, 66 years old, lived in Fangjiazhuang village, gate house town, Fushan District, Yantai, Shandong Province. He went to Yantai Hill Hospital for examination in March 2008 because of abdominal pain, increased abdominal distension, feeding difficulties and diagnosed with stomach cancer at the pylorus, with the size of about 3.5 cm×3.0 cm. At that time, He got better by surgery excision and the following chemotherapy. In May 2009, he felt unwell once again with increased abdominal pain and chest tightness, and then he went to Yantai Yuhuangding Hospital. Diagnostic ultrasound and X-ray examination showed multiple hypoechoic liver nodules were present, and the larger were about 2.8 cm×2.3 cm in size, lung markings were increased, and nodular density shadow was seen in the right middle upper lung field with blurred edges. This suggested the metastatic lesions in liver and lung. On Jun. 28, 2009, he took the medicine according to the invention for treatment. After five days, his appetite began to get better and urine output was increased, as well as bowel movements began to be regular and sleep got better. After seven days, the edema began to subside, and the pain began to reduce. 15 days later, his diet began to be come regular, urine and bowel movement became normal. One month later, all symptoms of the body basically disappeared except that he had vague abdominal pain occasionally. Two months later, he felt no discomfort and his life returned to normal. Also, he looked health and gained 5.9 kg of weight. Further he could do some housework or light physical work as normal. After treatment for further one month, he went to the hospital and accepted CT examination, the results showed the liver, gallbladder, lung, pleura and ribs were all normal in location and shape. Two months of consolidation therapy later, the medicine-taking discontinued. He fully recovered after a total of five months of treatment and could work and live as normal person, as well as in the whole course of treatment, no side effects occurred. So far, he has been in good physical condition.

Case 3.

Zhang Shu-Ying, female, 85 years old, lived in nursing home, gate house town, Yantai City, Shandong Province. She went to the hospital due to a nodule pain at right side of the neck in March 2007 and diagnosed with arterial aneurysm. At that time, the hospital was unable to conduct surgical resection for her since she is too old and the hemangioma on the right carotid artery was too close to her heart. Moreover, there was no effective drug in the hospital, thus the elderly woman had to come back to nursing home. As the tumor increased year in year from a small nodule to an egg-sized large tumor, the pain gradually increased. The elderly woman could not bear and once thought of suicide several times, but she was afraid to bring trouble to the Presidency of the nursing home due to her suicide, thus she has borne the pain over the 2 years. Finally on Jul. 12, 2009, a volunteer named Wang knew about her illness and bought the medicine composition of this invention for her. The elderly woman felt that the pain was reduced only on the fifth day after taking the medicine. On the eighth day, the tumor was seen to become smaller. A month later, it was seen that the tumor was changed from egg size to egg yolk size, and neck pain was gone, except that she still felt some local fullness. After treatment for further one month, swelling disappeared and there was no local discomfort, the elderly woman had a good appetite and sleep, as well as she looked healthy and could look after herself. One month of consolidation therapy later, the medicine-taking was discontinued. She fully recovered after a total of three months of treatment, and in the whole course of treatment, no side effects occurred. So far, she has been in good physical condition.

Case 4.

Sun Ji-Fu, male, 48 years old, lived in Yuankou village, Zhanggezhuang town, Fushan District, Yantai City, Shandong Province. He went to Yantai Yuhuangding Hospital for examination and diagnosed with liver cancer, the biggest one was of a size of 6.0 cm×5.5 cm. At that time, he decided to accept surgical resection due to his good physical condition, but the surgery failed to continue since the abdominal cavity was found to be filled with abdominal mass, at last the abdominal cavity was sutured and maintained intact, and he was informed that the tumor has been resected. After coming back home, his condition has never got better.

On Jul. 3, 2009, Sun Ji-Fu started to take medicine composition of the present invention for treatment. 3 days after drug administration, his appetite and frequency of urination began to improve. 5 days later, the pain began to reduce, edema began to reduce, and bowel movement began to become regular. 7 days later, his sleep was significantly improved and 15 days later pain was reduced and painkillers were seldom required. 1 month later, all symptoms were relieved, his looks began to get better, his strength was increased, and he could do some adequate exercise. 2 months later, he gained 2.5 kg of weight, his strength was increased significantly, his looks were obviously improved, except that there was still dull pain in abdominal region occasionally, no other abnormal symptoms were found. After another one month treatment, he went to the hospital and accepted CT examination, the results showed there exited 1.6 cm×1.2 cm hypoechoic nodules in liver, and lung, gallbladder, spleen and kidneys were normal. After treatment with the medicine composition of the invention for further 1 month, the CT examination showed liver, lung, gallbladder, spleen and kidneys were normal, and he was in a good physical condition, the diet was normal, the uterine and bowel movement were normal, further he felt no discomfort, looked healthy and gained 6 kg of weight. Moreover, his strength restored normal and could work and live as normal. 2 months of consolidation therapy later, the medicine-taking was discontinued. He fully recovered after a total of six months of treatment, and in the whole course of treatment, no side effects occurred. So far, he has been in good physical condition.

Case 5.

Teng Gui-Feng, female, 60 years old, lived in Chongyi village, Gate house town, Fushan District, Yantai, Shandong Province. She went to Yantai Yuhuangding Hospital for examination on Mar. 17, 2008 due to chest tightness, cough, night sweats, loss of appetite, weight loss, physical weakness. CT examination revealed that the thorax was symmetric, irregular mass shadow was seen on the posterior basal segment of lower lobe of the right lung with the size of about 2.3 cm×1.4 cm×5 cm, lobulation was deep, edges were still smooth and stretched with pleura. Irregular clumps were seen in the lower mediastinum on the left margin of nodules, with the size of about 6.7 cm×5.7 cm and irregular shape, the size and shape of the heart were normal, there was no pericardial effusion, vascular thickness was seen to be uniform without abnormal changes, right pleura thickened, and there were no pleural effusion and pneumatosis. The lesion was found too large after conducting thoracotomy in the hospital, and could not be resected considering the big vessels, pathology showed "small cell lung cancer." On Jun. 25, 2008, she started to take the medicine of this invention. On the fifth day, cough was reduced, appetite was improved, bowel movement was unobstructed, and sleep was improved. 15 days later, cough disappeared, the body had got relaxed feeling. A month later, all symptoms apparently disappeared, diet became regular, sleep was good, physical strength was increased, and she could do housework. After further 2 months of medication, she went to the hospital to conduct CT examination, the report showed that, bilateral thoraxes were symmetric, mediastinal trachea had no significant shift, double lower lung showed patchy shadow and increase in lung opacity (obvious on the right), 3.5 cm×2.6 cm low-density nodules were still slightly visible within the mediastinum, it had unclear boundaries with esophagus. The shadow of swelling lymph nodes was seen within mediastina, subcarinal lymph nodes were around 0.7 cm×1.2 cm, the plaque-like high density calcified lesions could be seen in the surrounding area, and calcified lesions could be seen on left coronary artery and bronchial wall. Two further months after the use, she went to the hospital and conduct CT examination, the results indicated that bilateral thoraxes were symmetric, the indicated ribs were normal, the lungs were normal in size and shape, there was no effusion in the bilateral pleural cavities, no banners were raised on both sides, and liver and gallbladder were normal in size and shape. Also she was in a good physical condition, the diet was normal, the uterine and bowel movement was normal, further he felt no discomfort, looked healthy and gained 7.5 kg of weight. Moreover, his strength restored normal and could work and live as normal. 2 months of consolidation therapy later, the medicine-taking was discontinued. He fully recovered after a total of seven months of treatment, and in the whole course of treatment, no side effects occurred. So far, he has been in good physical condition.

Case 6.

Liu Yu-Cui, female, 53 years old, lived in Louzikou village, Zhanggezhuang town, Zhang Fushan District, Yantai City, Shandong Province. She went to the hospital for examination three years ago because of chest tightness, abdominal distension and weakness and diagnosed with leukemia (CML). Over three years, she had been treated with imported drugs and dare not to stop drug-taking. In the middle of the three years, she once stopped to take medicine for half one month, but the disease relapsed and became more severe. Since then, she dare not to stop and has taken the imported drugs for three years, but she had not recovered. Moreover, since drug side effects of systemic edema, constant chest pain and weakness, she started to take the medicine of this invention on Jul. 1, 2009. Three days later, her appetite began to improve and the urine also began to increase. 7 days later, she felt the facial edema began to dissipate. 15 days later, systemic edema began to subside. 1 month later, the edema disappeared and his facial looks got better, his diet was regular, the urine and bowel movement was unobstructed, his strength increased and he gained 1.5 kg of weight. She then went to Yantai Yuhuangding Hospital for complete blood examination, the reports showed that, the white blood cells and red blood cells were normal in every aspect, only the mean corpuscular volume was 99.3↑, mean corpuscular hemoglobin was 35.6↑, mononuclear cells percentage was 10.2↑. eosinophil percentage was 0.3↑, eosinophil absolute value was 0.02↑, other values were all normal. After another one month of therapy, she went again to Yantai Yuhuangding Hospital for complete blood examination, only the average hemoglobin concentration was 372↑, other values of leukocyte and erythrocyte were in the normal range. Moreover, she was in a very good physical condition, her diet was normal, the uterine and bowel movements were normal, also he slept well, looked healthy and gained 16.5 kg of weight. Moreover, her strength totally restored normal and could do any heavy work. One month of consolidation therapy later, the medicine-taking was discontinued. She fully recovered after a total of three months of treatment, and in the whole course of treatment, no side effects occurred. So far, she has been in good physical condition.

Case 7.

Bao De-Yun, female, 46 years old, lived in Xie village, Huili town, Fushan District, Yantai, Shandong Province. She was diagnosed with breast cancer in Yantai Cancer Hospital on Jan. 25, 2009. The CT examination showed that, a hypoechoic mass could be detected on upper outer quadrant of right breast, with the size of about 5.0 cm×1.8 cm and ill-defined boundaries. In combination with pathological examination, it was showed that she suffered from right breast cancer. After surgical resection and the following chemotherapy, she went out of hospital in Mar. 24, 2009, and insisted on doing chemotherapy. On Jul. 18, 2009, her condition suddenly worsened with the poor spirit and poor appetite, and she could not turn over in bed and look after herself. X-ray and ultrasound diagnostic results in Yantai Yuhuangding Hospital suggested that multiple hypoechoic nodules were seen on the liver with the larger nodule of about 2.5 cm×2.0 cm, indicating metastatic lesions, and lung markings increased, nodular density shadow was seen in the right upper lung field with blurred boundaries, suggesting the right lung lesions. On Aug. 2, 2009, she started taking the medicine of this invention for treatment, 3 days later, her appetite began to slowly increase and urine increased. 5 days later, the bowel movement began to be unobstructed. 7 days later, her sleep was improved and the pain was relieved. 15 days later, she could stand up out of bed to walk. 20 days later, she could take care of herself. 1 months later, her looks began to get better, she gain 3 kg of weight with increased strength and could do housework. After she went to the hospital for ultrasound examination, the results indicated that liver shows a hypoechoic node in size of 1.7 cm×1.2 cm. After another one month therapy, she went again to the hospital for ultrasound examination, the results showed, the liver was normal in size and shape, the real echo was uniform, indicating she was in a normal physical condition. Two months of consolidation therapy later, the medicine-taking was discontinued. She fully recovered after a total of four months of treatment, and in the whole course of treatment, no side effects occurred. So far, she has been in good physical condition.

The Chinese medicine composition of the present invention is in the form of oral solution, and may be taken twice per day with 50 ml each time. After the Chinese medicine composition is considerably concentrated, the administration dose could be reduced. Each period of treatment is 30 days.

EXAMPLES

The formulation of the Chinese medicine composition of examples 1-5 of the invention is shown in Table 1 below.

TABLE 1

| Chinese medicines | Seq. ID examples | | | | |
| --- | --- | --- | --- | --- | --- |
| | 1 | 2 | 3 | 4 | 5 |
| turtle shell | 10 | 15 | 20 | 25 | 30 |
| radix ranunculi ternati | 15 | 20 | 22 | 25 | 30 |
| rhizoma dioscoreae bulbiferae | 10 | 11 | 12 | 13 | 15 |
| concha arcae | 10 | 15 | 20 | 25 | 30 |
| fructus ligustri lucidi | 10 | 11 | 12 | 13 | 15 |
| cordyceps sinensis | 10 | 11 | 12 | 13 | 15 |
| dwarf lilyturf tuber | 10 | 11 | 12 | 13 | 15 |
| lilium brownii | 10 | 15 | 20 | 25 | 30 |
| radix astragali | 10 | 11 | 12 | 13 | 15 |
| angelica sinensis | 5 | 6 | 7 | 8 | 10 |
| radix pseudostellariae | 10 | 15 | 20 | 25 | 30 |
| spina date seed | 10 | 12 | 14 | 16 | 18 |
| fruit-spike of common selfheal | 10 | 11 | 12 | 13 | 15 |
| pericarpium citri reticulatae | 3 | 5 | 7 | 8 | 10 |
| costustoot | 3 | 5 | 7 | 8 | 10 |
| cape jasmine fruit | 3 | 5 | 7 | 8 | 10 |
| radix scrophulariae | 10 | 11 | 12 | 13 | 15 |
| radix rehmanniae | 10 | 15 | 20 | 25 | 30 |
| rhizoma corydalis | 5 | 6 | 7 | 8 | 10 |
| safflower | 5 | 6 | 7 | 8 | 10 |
| turmeric root-tuber | 6 | 7 | 8 | 10 | 12 |
| cortex moutan | 6 | 7 | 8 | 10 | 12 |
| concha ostreae | 10 | 15 | 20 | 25 | 30 |
| poria cocos | 10 | 11 | 12 | 13 | 15 |
| herba lysimachiae | 30 | 35 | 40 | 50 | 60 |
| the root of red-rooted salvia | 5 | 7 | 9 | 13 | 15 |
| isatis indigotica fort | 10 | 11 | 12 | 13 | 15 |
| honeysuckle | 10 | 11 | 12 | 13 | 15 |
| fructus forsythiae | 6 | 8 | 10 | 12 | 15 |
| cortex eucommiae | 10 | 11 | 12 | 13 | 15 |
| radix gentianae macrophyllae | 5 | 6 | 7 | 8 | 10 |
| radix paeoniae alba | 15 | 20 | 25 | 27 | 30 |
| subprostrate sophora | 6 | 7 | 8 | 9 | 10 |

TABLE 1-continued

| Chinese medicines | Seq. ID examples | | | | |
|---|---|---|---|---|---|
| | 1 | 2 | 3 | 4 | 5 |
| seman platycladi | 10 | 12 | 14 | 16 | 18 |
| snakegourd fruit | 10 | 13 | 15 | 18 | 20 |
| membrane of chicken gizzard | 5 | 6 | 7 | 8 | 10 |
| platycodon grandiflorum | 5 | 6 | 7 | 8 | 10 |
| radix liquiritiae | 5 | 6 | 7 | 8 | 10 |

The Chinese medicines of the above Table 1 may weight in a unit of kilogram (kg).

The medicines are weighed in proportion, placed into a medicine pot, immersed by adding water, and decocted through conventional methods. The resulting decoction is concentrated and made into concentrated solution, followed by split charging, it also could be processed into honeyed pills, granules, injection, etc.

What is claimed is:

1. A composition for treating tumors in a subject in need thereof, wherein the tumors are caused by pancreatic, stomach, breast, or liver cancer, leukemia, lung or liver metastasis, and/or arterial aneurysm, said composition comprising:
    i.) turtle shell in an amount of 10-30 parts by weight;
    ii.) radix ranunculi ternati in an amount of 15-30 by weight;
    iii.) rhizoma dioscoreae bulbiferae in an amount of 10-15 parts by weight;
    iv.) concha arcae in an amount of 10-30 parts by weight;
    v.) fructus ligustri lucidi in an amount of 10-15 parts by weight;
    vi.) cordyceps sinensis in an amount of 10-15 parts by weight;
    vii.) dwarf lilyturf tuber in an amount of 10-15 parts by weight;
    viii.) lilium brownii in an amount of 10-30 parts by weight;
    ix.) radix astragali in an amount of 10-15 parts by weight;
    x.) angelica sinensis in an amount of 5-10 parts by weight;
    xi.) radix pseudostellariae in an amount of 10-30 parts by weight;
    xii.) spina date seed in an amount of 10-18 parts by weight;
    xiii.) fruit-spike of common selfheal in an amount of 10-15 parts by weight;
    xiv.) pericarpium citri reticulatae in an amount of 3-10 parts by weight;
    xv.) costustoot in an amount of 3-10 parts by weight;
    xvi.) cape jasmine fruit in an amount of 3-10 parts by weight;
    xvii.) radix scrophulariae in an amount of 10-15 parts by weight;
    xviii.) radix rehmanniae in an amount of 10-30 parts by weight;
    xix.) rhizoma corydalis in an amount of 5-10 parts by weight;
    xx.) safflower in an amount of 5-10 parts by weight;
    xxi.) turmeric root-tuber in an amount of 6-12 parts by weight;
    xxii.) cortex moutan in an amount of 6-12 parts by weight;
    xxiii.) concha ostreae in an amount of 10-30 parts by weight;
    xxiv.) poria cocos in an amount of 10-15 parts by weight;
    xxv.) herba lysimachiae in an amount of 30-60 parts by weight;
    xxvi.) root of red-rooted salvia in an amount of 5-15 parts by weight;
    xxvii.) isatis indigotica fort in an amount of 10-15 parts by weight;
    xxvii.) honeysuckle in an amount of 10-15 parts by weight;
    xxix.) fructus forsythiae in an amount of 6-15 parts by weight;
    xxx.) cortex eucommiae in an amount of 10-15 parts by weight;
    xxxi.) radix gentianae macrophyllae in an amount of 5-10 parts by weight;
    xxxii.) radix paeoniae alba in an amount of 15-30 parts by weight;
    xxxiii.) subprostrate sophora in an amount of 6-10 parts by weight;
    xxxiv.) seman platycladi in an amount of 10-18 parts by weight;
    xxxv.) snakegourd fruit in an amount of 10-20 parts by weight;
    xxxvi.) membrane of chicken gizzard in an amount of 5-10 parts by weight;
    xxxvii.) platycodon grandiflorum in an amount of 5-10 parts by weight;
    xxxviii.) parts of radix liquiritiae in an amount of 5-10 parts by weight.

2. The composition claim 1, wherein the composition is in a form of a concentrated oral solution.

* * * * *

UNITED STATES PATENT AND TRADEMARK OFFICE
CERTIFICATE OF CORRECTION

PATENT NO. : 8,414,937 B2  
APPLICATION NO. : 13/292395  
DATED : April 9, 2013  
INVENTOR(S) : Aiying Li Page 1 of 1

It is certified that error appears in the above-identified patent and that said Letters Patent is hereby corrected as shown below:

Title Page, Item (76) Inventor: Aiying Li, ~~Yantai~~ Yantai City (CN)

Title Page, Item (30) Foreign Application Priority Data

Sep. 9, 2011 (CN)........~~2011 1 0280960~~ 2011 1 0280960.4

Signed and Sealed this  
Eleventh Day of June, 2013

Teresa Stanek Rea  
*Acting Director of the United States Patent and Trademark Office*